United States Patent
Heinonen

(10) Patent No.: US 11,141,553 B2
(45) Date of Patent: Oct. 12, 2021

(54) VENTILATION CONTROL SYSTEM AND METHOD UTILIZING PATIENT OXYGEN SATURATION

(71) Applicant: General Electric Company, Schenectady, NY (US)

(72) Inventor: Erkki Paavo Olavi Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 236 days.

(21) Appl. No.: 16/032,699

(22) Filed: Jul. 11, 2018

(65) Prior Publication Data

US 2020/0016350 A1 Jan. 16, 2020

(51) Int. Cl.
*A61M 16/00* (2006.01)
*G16H 40/63* (2018.01)
*A61M 16/10* (2006.01)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ............ A61M 16/024; A61M 16/0003; A61M 16/0051; A61M 16/1005; A61M 16/0891; G16H 40/63
See application file for complete search history.

(56) References Cited

U.S. PATENT DOCUMENTS 8,251,914 B2 * 8/2012 Daniels ................. A61B 5/083
600/529
9,364,623 B2 * 6/2016 Lellouche ............ A61M 16/00
(Continued)

FOREIGN PATENT DOCUMENTS

EP 1984051 10/2008

OTHER PUBLICATIONS

Heinonen, "Ventilator System and Method for Controlling the Same to Provide Spontaneous Breathing Support", unpublished U.S. Appl. No. 15/423,340, filed Feb. 2, 2017.
(Continued)

*Primary Examiner* — Joseph D. Boecker
*Assistant Examiner* — Thomas W Greig
(74) *Attorney, Agent, or Firm* — Andrus Intellectual Property Law, LLP

(57) ABSTRACT

A patient ventilation system includes a ventilator configured to deliver ventilation gas to patient, a $CO_2$ concentration sensor configured to provide $EtCO_2$ measurements for the patient, and an $SpO_2$ monitor configured to determine an $SpO_2$ value for the patient. A ventilation control module is executable on a processor and configured to compare the $SpO_2$ value to a threshold $SpO_2$ and determine from this comparison that the $SpO_2$ value indicates inadequate oxygenation. A minimum ventilation amount is then set, and the ventilator is then controlled based on the $EtCO_2$ measurements and the minimum ventilation amount so as to deliver at the least the minimum ventilation amount to the patient while the $SpO_2$ value indicates inadequate oxygenation.

20 Claims, 3 Drawing Sheets

(52) U.S. Cl.
CPC .............. *A61M 2016/0027* (2013.01); *A61M 2016/103* (2013.01); *G16H 40/63* (2018.01)

(56) References Cited

U.S. PATENT DOCUMENTS

| | | | | |
|---|---|---|---|---|
| 2002/0112726 | A1* | 8/2002 | Schmidt | A61M 16/0677 128/204.23 |
| 2008/0236582 | A1* | 10/2008 | Tehrani | A61M 16/024 128/204.22 |
| 2008/0295839 | A1* | 12/2008 | Habashi | A61M 16/0069 128/204.22 |
| 2011/0041849 | A1* | 2/2011 | Chen | A61B 5/14551 128/204.23 |
| 2011/0175728 | A1* | 7/2011 | Baker, Jr. | A61M 16/0063 340/540 |
| 2013/0263855 | A1* | 10/2013 | Tivig | A61M 16/10 128/204.23 |
| 2015/0018648 | A1* | 1/2015 | Boyer | A61M 16/0051 600/323 |
| 2015/0114395 | A1 | 4/2015 | Heinonen et al. | |
| 2016/0058346 | A1 | 3/2016 | Heinonen | |
| 2018/0099109 | A1* | 4/2018 | Kinsky | A61M 16/04 |

OTHER PUBLICATIONS

Sarkela et al., "Method and System for Controlling Patient Sedation and Spontaneous Breathing Intensity", unpublished U.S. Appl. No. 15/988,951.

* cited by examiner

VENTILATION CONTROL SYSTEM AND METHOD UTILIZING PATIENT OXYGEN SATURATION

BACKGROUND

This disclosure generally relates to methods and systems for controlling patient ventilation, and more specifically to methods and systems for controlling ventilation based on $EtCO_2$ and patient oxygen saturation.

Ventilation amount is controlled to maintain an appropriate $CO_2$ level for the patient. Measured end-expiratory $CO_2$ ($EtCO_2$) concentration is used as indicator of the $CO_2$ level. A typical $EtCO_2$ value is around 5-6 kPa but in certain circumstances the optimum value may deviate from this. Metabolism and $CO_2$ production vary between subjects. This depends, for example, on subject size, age, gender, anxiety level, etc. The anxiety varies during the mechanical ventilation and also treatment actions vary the required $CO_2$ clearance. To maintain the optimal subject $CO_2$ level the ventilation amount must be tuned. Ventilation amount, such as ventilation rate or breath volume, can be regulated automatically to maintain the given target patient $CO_2$ level exploiting the measured $EtCO_2$ value to control ventilation amount to match the measured value with given target.

Current medical monitoring technology measures $CO_2$ concentrations in breathing gas expired by the patient ($EtCO_2$) to gauge arterial $CO_2$ concentrations. The international standards set for anesthesia delivery and non-invasive critical care ventilation systems mandate the use of expired $CO_2$ ($EtCO_2$) monitoring when a patient is undergoing anesthesia. The rationale is that during anesthesia the $EtCO_2$ is a surrogate for, or estimate of, patient arterial blood $CO_2$ partial pressure ($PaCO_2$). However, the relationship between $EtCO_2$ and $PaCO_2$ is not always direct or as expected, especially in situations involving patients with pulmonary impairments or cardiac conditions.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a patient ventilation system includes a ventilator configured to deliver ventilation gas to patient, a $CO_2$ concentration sensor configured to provide $EtCO_2$ measurements for the patient, and an $SpO_2$ monitor configured to determine an $SpO_2$ value for the patient. A ventilation control module is executable on a processor and configured to compare the $SpO_2$ value to a threshold $SpO_2$ and determine that the $SpO_2$ value indicates inadequate oxygenation. A minimum ventilation amount is then set, and the ventilator is then controlled based on the $EtCO_2$ measurements and the minimum ventilation amount so as to deliver at the least the minimum ventilation amount to the patient while the $SpO_2$ value indicates inadequate oxygenation.

In one embodiment, a method of controlling a ventilator to ventilate a patient includes receiving an $EtCO_2$ for the patient from a $CO_2$ concentration sensor and receiving an $SpO_2$ value for the patient from an $SpO_2$ monitor. The method includes, at a processor executing a ventilation control module, comparing the $SpO_2$ value to a threshold $SpO_2$ and determining that the $SpO_2$ value indicates inadequate oxygenation. The ventilator is controlled based on the $EtCO_2$ measurements and the minimum ventilation amount so as to deliver at least the minimum ventilation amount to the patient while the $SpO_2$ value indicates inadequate oxygenation.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
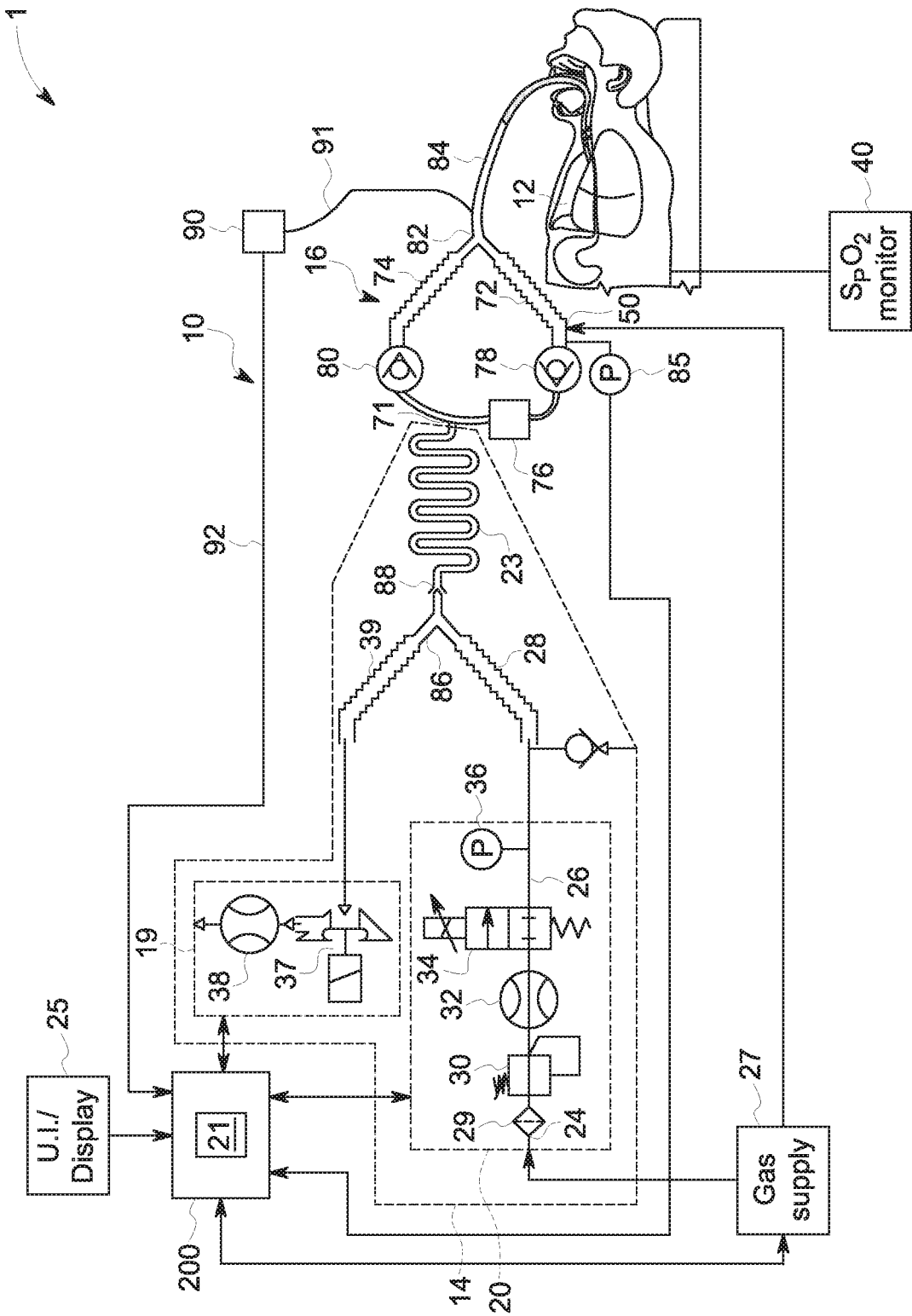
FIG. 1 is a schematic drawing of a patient ventilation system according to the present disclosure.

Automatic ventilation control adjusts ventilation amount automatically to reach and maintain a target $EtCO_2$ using $EtCO_2$ measurements from the subject in a closed loop control algorithm. The inventor has recognized that such automatic, closed loop control systems involve a risk involved to situation where measured $EtCO_2$ deviates from actual blood $CO_2$ levels. For example, measured $EtCO_2$ levels may diverge from actual blood $CO_2$ levels in situations where the regional spread of ventilation and perfusion of the lungs diverge from each other. In such situations, alveolar gas exchange degrades, and thus the $EtCO_2$ output of the lungs does not correspond with the patient's $PaCO_2$. This ventilation mismatch occurs, for example, where a patient suffers a large alveolar dead-space caused by e.g. pulmonary embolism or major pulmonary shunt. In these circumstances the measured $EtCO_2$ can be much lower than the blood $CO_2$ level—i.e., the $EtCO_2$ does not match the patient arterial blood $CO_2$ partial pressure ($PaCO_2$) but can be less than half or even one third of the $PaCO_2$ value.

Less traumatic causes of mismatch between $EtCO_2$ and blood $CO_2$ levels are also possible, such as atelectasis where alveoli collapse in perfused sections of the lungs. Atelectasis can occur in situations where a patient is being ventilated with high oxygen levels and/or during periods of extended ventilation of an immobile patient. Additionally, patients with certain medical conditions may have a higher tendency for mismatch between measured $EtCO_2$ and actual blood $CO_2$ levels. For instance, $EtCO_2$ measurements for obese patients tend to be less accurate estimations of blood $CO_2$ than for non-obese patients. Certain pulmonary conditions may also cause such a mismatch. In addition to pulmonary causes, another reason for mismatch between $EtCO_2$ and blood $CO_2$ levels is due to perfusion issues, such as cardiac issues. Cardiac issues, for example, may cause a decreased blood pressure or blood flow to the lungs, and insufficient gas exchange may occur due to insufficient perfusion to the lungs. Thus, the carbon dioxide is not being sufficiently removed from the blood and the blood carbon dioxide may be increasing.

In all of these situations, where $EtCO_2$ does not accurately reflect the blood $CO_2$, controlling ventilation based on the mismatched $EtCO_2$ level can be problematic for the patient. Where $EtCO_2$ levels are artificially low, controlling the ventilator based on the $EtCO_2$ causes an inappropriate decrease in ventilation amounts supplied to the patient. If not compensated with increased breathing gas oxygen concentration, the decreased ventilation amount may cause an insufficient amount of oxygen delivery to the patient. And if such compensation results to very high breathing gas oxygen concentration, oxygen delivery may degrade further due to resulting atelectasis increasing the shunt perfusion. Namely, during ventilation of a patient with normal pulmonary and perfusion function where the low $CO_2$ level is caused by a real reduced patient metabolism, the natural and correct ventilation control reaction is to decrease patient ventilation amount to allow the $CO_2$ level to increase back into the normal range. However, in a patient with compromised pulmonary or perfusion function, such a decrease in ventilation reduces the amount of available oxygen for the patient's already-compromised gas exchange. This can worsen the patient's already low blood oxygen levels, with undesired consequences to patient.

In view of the foregoing problems and issues with automatic ventilation control systems, the inventor has developed the disclosed system and method that utilizes blood oxygen saturation measurements to supplement and modify the $EtCO_2$ control algorithm based on oxygen saturation measurements for a patient so that inappropriate ventilation reductions do not occur. In one example, patient ventilation is controlled based on peripheral capillary oxygen saturation ($SpO_2$) measurements by a pulse oximetry monitor and $EtCO_2$ measurements for the patient where the automatic ventilation control based on $EtCO_2$ is modified if the arterial oxygen saturation level becomes reduced. For example, if an $SpO_2$ value indicates inadequate oxygenation in comparison with a defined threshold $SpO_2$, then a minimum ventilation amount representing ventilation amount when the SpO2 value indicated adequate oxygenation in comparison with the threshold may be set to prevent any ventilation reduction below the minimum set ventilation amount.

The inventor has also recognized that problems may occur where $SpO_2$ measurements from a pulse oximeter may become unreliable. Pulse oximeters are sensitive to measurement artifacts, such as noise introduced due to movement of the patient or reduced peripheral perfusion at the measurement site. Through experimentation and research in the relevant field, the inventor has recognized that artifacts have a tendency to artificially suppress, or decrease, $SpO_2$ measurement value, and that $SpO_2$ values above a normal $SpO_2$ threshold (such as 90) tend to reflect accurate $SpO_2$ measurements not unduly influenced by artifact. Accordingly, the inventor has recognized, because of body oxygen buffering storages, $SpO_2$ value exceeding the $SpO_2$ threshold may be utilized for ventilation control over a predetermined amount of time. For example, the system may utilize $SpO_2$ value indicating adequate oxygenation over a predetermined amount of time prior to setting the minimum ventilation amount. This provides a robust ventilation control system for avoiding improper ventilation reduction due to $EtCO_2$ mismatch that is not unduly influenced by noise in $SpO_2$ measurements.

FIG. 1 provides one embodiment of a patient ventilation control system 1 for controlling patient sedation and spontaneous breathing intensity. The system 1 includes a ventilator system 10 that provides an inspiration gas to the patient 12 utilizing a re-breathing system. The ventilator system 10 comprises a machine ventilator circuit 14 for assisting breathing functions of the patient, a breathing circuit 16 for connecting lungs of the patient and the machine ventilator circuit 14 to exchange the gas in the lungs, and ventilation control module 21 for controlling operation of the ventilator system 10 according to the patient's ventilation needs. The ventilator system 10 shown in FIG. 1 includes a gas supply 27 for supplying breathing gases to the patient, which include a fresh gas, oxygen ($O_2$), and/or inhalational anesthetic agents, such as Desflurane, Isoflurane, nitrous oxide, Sevoflurane, Xenon, etc. The system 1 may further include a user interface 25 for entering any information needed while ventilating the patient, as well as for displaying patient information, including the spontaneous breathing intensity, measured $EtCO_2$ minute, and ventilation rate and other ventilation delivery information.

The machine ventilator circuit 14 generally comprises an inspiration delivery unit 20 for delivering the pressure support gas needed to enable an inspiration of the patient, an expiration circuit 19 for controlling a discharge of the expiration gas and a reciprocating unit 23 (e.g., a bellows and bottle combination where the bellows are arranged within the bottle, or a long gas flow channel as shown in FIG. 1 for compressing the gas under a control of the drive gas pressure towards lungs of the patient to facilitate the inspiration). In certain embodiments, both the inspiration delivery unit 20 and the expiration circuit 19 may be controlled by the computing system 200 executing the ventilation control module 21.

As illustrated in FIG. 1, the inspiration delivery unit 20 comprises a compressed gas interface 24 connected to a compressed gas supply 27. The compressed gas can be either oxygen or air. The inspiration delivery unit 20 also comprises a filter 29 for filtering impurities, a pressure regulator 30 for regulating a pressure of gases flowing from the gas interface, a flow sensor 32 for measuring an inspiration delivery flow from the gas interface and a flow control valve 34 for opening or closing the inspiration delivery flow. The flow sensor 32 and flow control valve 34 are each coupled to the computing system 200, to be received by the ventilation control module 21. Further, the inspiration delivery unit 20 may comprise a pressure sensor 36 for measuring the gas pressure flowing along the conduit 26 and an inspiration branch 28 towards the reciprocating unit 23. Thereby, the breath volume can be determined based on the gas flow and pressure. In other embodiments, the ventilation control module 21 may be configured and utilized in connection with an intensive care unit (ICU) ventilator, where the breathing circuit 16 is eliminated and the gas is delivered directly to the patient from connection point 88. In such an embodiment, two distinct inspiration control modules may be provided, one for controlling air delivery and the other for controlling $O_2$ delivery to the patient.

The gas supply 27 may supply fresh breathing gas to the gas outlet 50 in the breathing circuit. The gas supply 27 may include any number of one or more tanks or vessels containing gasses, which may be compressed gasses, to be delivered to the patient, such as oxygen, air, nitrous oxide, and/or volatile anesthesia agents. The gas supply 27 may further include a gas mixer to mix some or all of the various gasses being supplied to the patient, and may comprise any number of filters, pressure regulators, air flow sensors, and air flow control valves, etc. as is well known in the relevant art.

The breathing circuit 16, which is operably connected to the machine ventilator circuit 14 at a breathing circuit connection 71 and to the fresh gas outlet 50, comprises an inspiration limb 72 for an inspired gas, an expiration limb 74 for an exhaled gas, a carbon dioxide ($CO_2$) remover 76 such as $CO_2$ absorber to remove or absorb carbon dioxide from the exhaled gas coming from the patient 12, a first one-way valve 78 for an inspired gas to allow an inspiration through the inspiration limb 72, a second one-way valve 80 for an expired gas to allow an expiration through the expiration limb 74, a branching unit 82 (such as a Y-piece) having at least three limbs, one of them being for the inspired gas, a second one being for the expired gas and a third one being for both the inspired and expired gases and being connectable to by means of the patient limb 84 to the lungs of the patient 12. Also the breathing circuit may comprise a pressure sensor 85 for measuring a pressure of the breathing circuit 16.

During the inspiration phase of the machine ventilation the expiration circuit 19 of the machine ventilator circuit 14 closes the expiration valve 37, such as under the control of the ventilation control module 21. This guides the inspiration gas flow from the inspiration delivery unit 20 through the inspiration branch 28 of a gas branching connector 86 and through the connection 88 of the reciprocating unit 23 pushing the breathing gas out from the breathing circuit connection 71 to the breathing circuit 16. The inspiration gas delivery unit 20 controlled by the ventilation control module 21 delivers the gas flow either to reach the given gas volume or a pressure at breathing circuit measured. For this control, the flow sensor 32 for measuring the inspiration flow and the pressure sensor 85 of the breathing circuit 16 are used.

The ventilator system 10 also includes a gas analyzer 90 to measure the concentrations of various gasses in the expiration gas from the patient, including the $CO_2$ concentration indicated by an $EtCO_2$ measurement. Such analyzer can be either a side-stream type that suctions a sample gas stream through sampling line 91 for analysis, or a mainstream type where the analysis occurs in the gas stream in the patient limb 84. The analyzer communicates gas concentrations to the computing system 200 through communication line 92. Gas analyzer 90 can be of any known type able to measure particular gas concentrations. For example, the gas analyzer 90 may be an infrared absorption analyzer configured to measure $CO_2$ concentration in the gases exhaled by the patient 12.

In embodiments where respiration support is provided, the breathing circuit 16 and the patient lungs are pressurized. For the expiration under the control of the ventilation control module 21, the inspiration delivery flow control valve 34 is closed stopping the inspiration delivery and the expiration valve 37 is opened to allow the gas release from the expiration branch 39 of the drive gas branching connector 86 and further through the connection 88 from the reciprocating unit 23. This allows the pressure release and breathing gas flow from breathing circuit 16 and the lungs of the patient 12 to the reciprocating unit 23. The breathing gas flows from the patient 12 through the patient limb 84, the branching unit 82, the expiration limb 74, the second one-way valve 80 for the expired gas and the breathing circuit connection 71 to the reciprocating unit 23. The pressure release is controlled for a desired expiration pressure, such as a positive end expiration pressure (PEEP) target. For this control, the ventilation control module 21 uses the breathing circuit pressure measured by the pressure sensor 85 and the expiration valve 37. The expiration gas flow may be measured using the flow sensor 38 located at the outlet the expiration valve 37 as shown in FIG. 1 or at any location on the expiration pathway from patient limb 84 to the expiration valve 37. In other embodiments, the ventilation support is delivered to the patient to assist spontaneous breathing. Such support requires identification of the patient spontaneous action and regulation of supporting pressure to provide adequate ventilation amount for the patient's metabolic need.

The expiration circuit 19 comprises an expiration valve 37 for discharging the expiration gas and a flow sensor 38, which is optional, for measuring the flow discharged through the expiration valve 37. The expiration circuit is in flow connection along an expiration branch 39 with the reciprocating unit 23. Various methods for controlling the ventilator 10 based on the $EtCO_2$ value are well known in the art, and one exemplary method is shown and described at U.S. application Ser. No. 14/065,918, which is incorporated herein by reference in its entirety.

The system 1 further includes an $SpO_2$ monitor 40, such as a pulse oximeter configured to measure the patient's blood oxygenation and output an $SpO_2$ value for the patient. For example, the $SpO_2$ monitor may conduct reflective or transmissive $SpO_2$ measurements. For example, the $SpO_2$ monitor may have an $SpO_2$ sensor device that attaches to, e.g., a patient's finger to conduct transmissive $SpO_2$ measurements using red and infrared light detection, as is common in patient monitoring.

Figure 2:
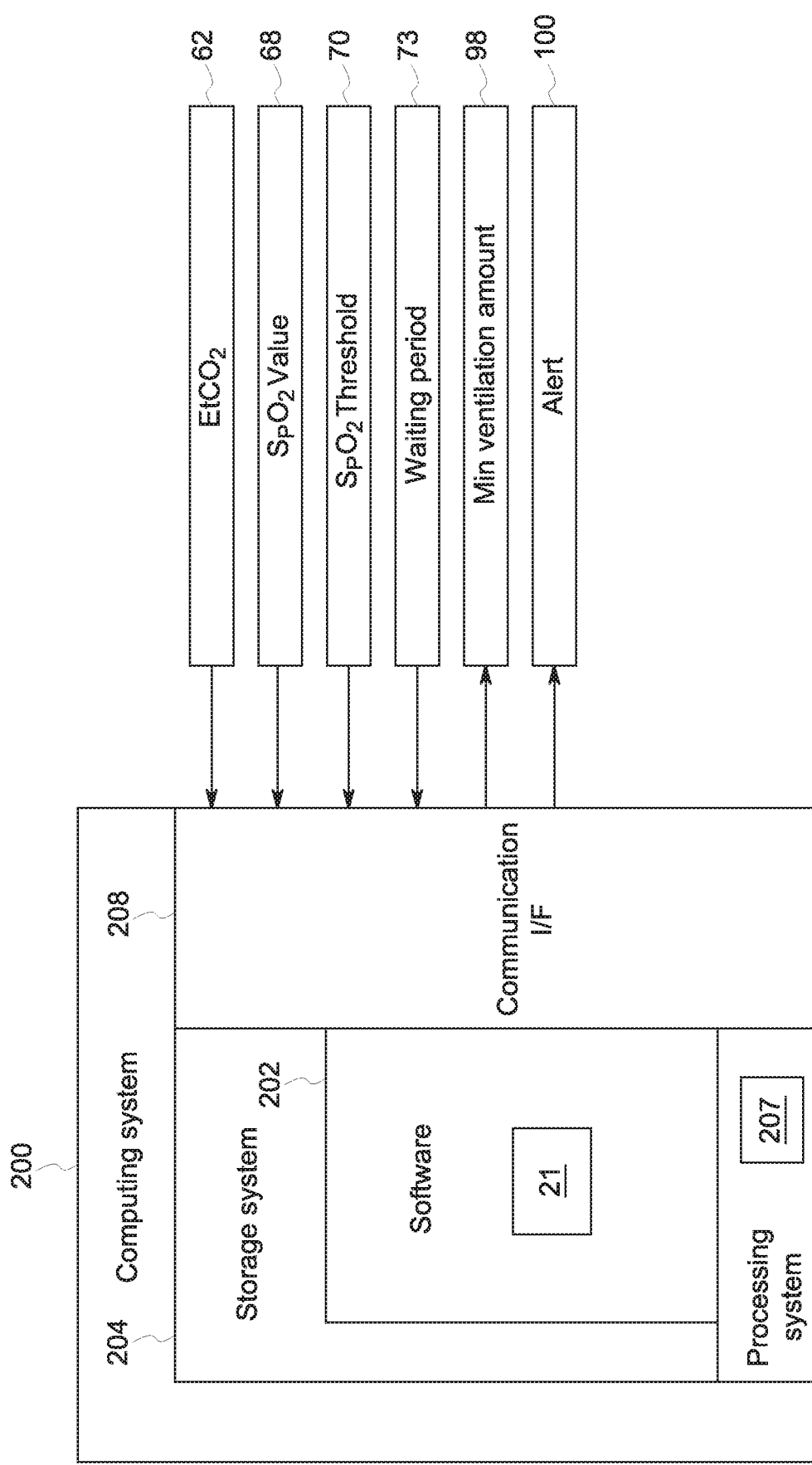
FIG. 2 is a schematic diagram of a computing system of the patient ventilation system according to the present disclosure.

With reference also to FIG. 2, a ventilation control module 21 may be configured and executable within the computing system 200 to control the ventilator 10 to set a minimum ventilation amount when the $SpO_2$ value 68 comparison with threshold $SpO_2$ 70 indicates inadequate oxygenation. Then the ventilation control module 21 executes steps to effectuate ventilation control such that a ventilation amount delivered to the patient is greater than or equal to the minimum ventilation amount 98. In certain embodiments, an alert 100 may be generated, such as via the user interface 25 associated with the ventilation system 10, to alert a clinician that the minimum ventilation control is in effect. Alternatively or additionally, the ventilation control module 21 may be configured to monitor the $SpO_2$ value and compare with the SpO2 threshold value for at least a predetermined waiting period 73 to determine that the $SpO_2$ value 68 continuously indicates inadequate oxygenation for the predetermined waiting period 73 prior to effectuating the minimum ventilation control.

Figure 3:
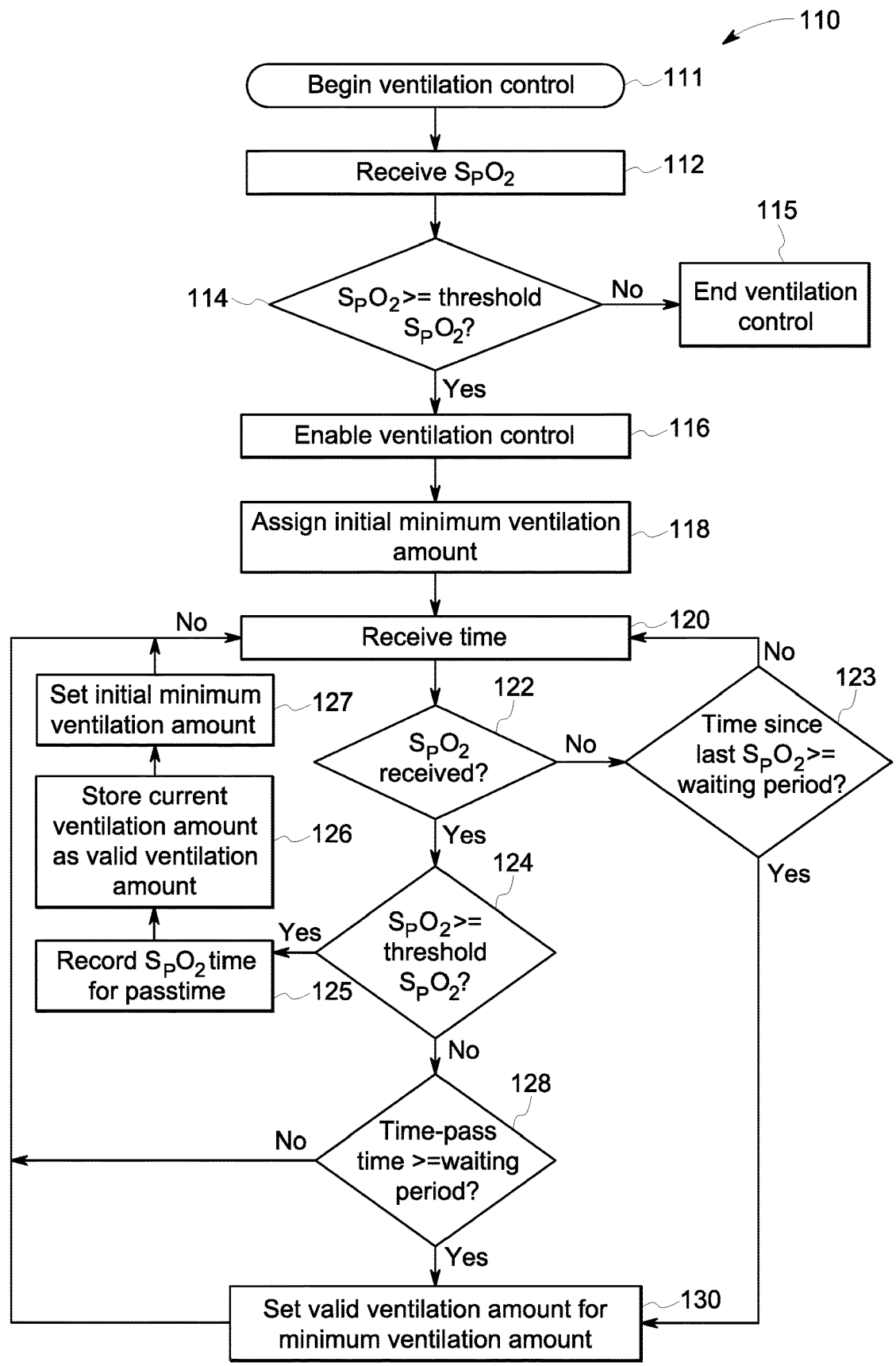
FIG. 3 is a flow chart depicting an exemplary method of controlling a ventilator to ventilate a patient according to the present disclosure.

FIG. 3 exemplifies one embodiment of a method 110 of controlling a ventilator 10. In the depicted embodiment, the ventilation control begins at step 111, such as upon initial operation of the ventilator with the patient or upon initial connection of the $SpO_2$ monitor. $SpO_2$ measurement is received at step 112 and compared to a threshold at step 114 to evaluate the adequacy of oxygenation status. If the comparison indicates inadequate oxygenation, the ventilation control based on $EtCO_2$ may not begin and the ventilation control method is terminated at step 115. Receiving $SpO_2$ indicating adequate oxygenation enables initiation of the $EtCO_2$ ventilation control (step 116). Thereafter, the ventilation control $SpO_2$ supervision ensures that the patient oxygenation status is running parallel to the ventilation control and, if deviation is detected, enacts a minimum ventilation amount determined for the patient. The supervision control inspects periodically whether a new $SpO_2$ is indicating adequate oxygenation is received within the time from the previous legitimate $SpO_2$ value.

Optionally, an initial minimum ventilation amount may be assigned at step 118, which may be a default value or a clinician-set value. The minimum ventilation amount may be a constant value set, for example, based on a patient's health or demographic information, or may be a preset value (which may even be zero). The supervision control then inspects periodically with comparison to the threshold SpO2 whether a new $SpO_2$ indicating adequate oxygenation is received within the time from the previous legitimate $SpO_2$ value. In FIG. 3, a time is received at step 120, and then the module waits for a subsequent $SpO_2$ value at step 122. Exceeding the waiting period results assigning the latest ventilation amount stored when $SpO_2$ indicated adequate oxygenation, which in this embodiment is at or above the $SpO_2$ threshold for the ventilation controller use, which is enacted at step 130. Once received, the $SpO_2$ is compared with the threshold $SpO_2$ at step 124. If this comparison is not below the threshold, and thus indicates adequate oxygenation, the receiving time and ventilation amount at the respective time are stored in memory at steps 125-126. The optional initial minimum ventilation amount is assigned for the ventilation controller use at step 127. If instead, at step 124 the $SpO_2$ comparison with the threshold indicates inadequate oxygenation, the elapsed time since the latest $SpO_2$ indicating adequate oxygenation is inspected against the waiting period at step 128. If that is less, the supervision control continues to search for new $SpO_2$ value until the expiration of the waiting period. If the waiting time is exceeded, the latest minimum ventilation amount stored when $SpO_2$ indicated adequate oxygenation by exceeding the threshold is set for the ventilation controller use.

The threshold $SpO_2$ may be a standard preset value indicating low blood-oxygen levels. To provide one example, the $SpO_2$ threshold 70 may be set at 90%; however, in other examples the $SpO_2$ threshold 70 may be set at some other value greater than or less than 90%, such as based on the environment in which the ventilator 10 is being operated (e.g. surgery, cardiac ICU, etc.) and patient condition. In certain embodiments, the threshold $SpO_2$ 70 may be clinician-set value, such as received via the user interface 25 associated with the ventilator 10. For example, the system 1 may be configured to allow clinicians to set threshold $SpO_2$ values 70 above or below a default threshold $SpO_2$ so as to conform operation of the system 1 to a particular environment or patient, and to avoid excessively activating the minimum ventilation control.

When received SpO2 indicates inadequate oxygenation, the minimum ventilation amount will be larger than or equal to the initial minimum ventilation amount. This limits the ventilation control operation range at the small ventilation amounts. Even during this limited ventilation control, the ventilator can increase the ventilation amount delivered in response to an increase in $EtCO_2$. Thus, if the $EtCO_2$ value increases, indicating intensifying metabolism of the patient, ventilation can be increased in accordance with normal control algorithms increasing CO2 clearance and oxygen delivery. If the $EtCO_2$ value then decreases in response to a metabolic decrease, such as a return back to a normal metabolic level for the patient, the system decreases the ventilation amount supplied to the patient in accordance with the decrease in $EtCO_2$, except that the ventilation amount is not permitted to become less than the minimum ventilation amount assigned for the ventilation controller allows. As will be understood by a person having ordinary skill in the art in light of this disclosure, the minimum ventilation amount may take any of various forms depending on the operation of the control system for the ventilator 10, such as a minimum minute ventilation amount, a minimum ventilation rate, a minimum effective alveoli minute ventilation, a minimum target breath volume, a minimum target alveoli breath volume, etc.

As described above, $SpO_2$ monitoring is prone to interference, and that noise factors tend to drive the $SpO_2$ signal below the $SpO_2$ values indicating normal healthy blood oxygenation levels. Accordingly, the ventilation control module 21 may be configured to monitor the $SpO_2$ for a predetermined waiting period 73 prior to effectuating the limited ventilation control mode. In other embodiments, ventilation control module 21 may be configured to automatically conduct the waiting period analysis prior to effectuating the limited ventilation control mode. Because the human body also has some oxygen reserve, the system may be configured to allow some time for measuring a $SpO_2$ value 68 indicating adequate oxygenation. To provide one example, the predetermined waiting period 73 may be one minute, but in other examples could be less than one minute or greater than one minute. For instance, the predetermined waiting period 73 may be a value between thirty seconds and ninety seconds. Depending on patient condition, allowing longer waiting period may already risk patient oxygenation. In certain embodiments, the predetermined waiting period 73 may be a clinician-set value, which can be chosen by the clinician to reflect certain monitoring environments and/or patient conditions.

In certain embodiments, if the limited ventilation control mode is effectuated, an alert may then be generated indicating the limited ventilation control mode has been effectuated. The alert may also indicate that the $SpO_2$ value may be unreliable, thus indicating to the clinician to check the $SpO_2$ sensor to determine whether the low $SpO_2$ is due to improper sensor placement, patient motion, etc.

In other embodiments, the minimum ventilation amount may be set based on historical ventilation information for the patient, such as picked from the ventilation history before the decline in the measured oxygen saturation was detected. The ventilation control module 21 may execute various instructions to review the historical ventilation information, utilizing various methods to locate an acceptable ventilation amount yielding an $SpO_2$ value that indicates adequate oxygenation. The historical ventilation information includes previous ventilation amounts delivered to the patient and corresponding $SpO_2$ values, which are correlated in time to the delivered ventilation amounts. The minimum ventilation amount is then set equal to the acceptable ventilation amount. The system then effectuates the limited ventilation control mode, such as by executing steps 116-130 of the method exemplified at FIG. 3.

FIG. 2 provides a system diagram of an exemplary computing system 200 incorporated in a system 1 for controlling the ventilator system 10. The exemplary computing system 200 includes a ventilation control module 21, which is a software module executable as described herein. The computing system 200 includes a processing system 206, storage system 204, software 202, and a communication interface 208. The processing system 206 loads and executes software 202 from the storage system 204, including the ventilation control module 21 which is an application within the software 202. The module 21 includes computer-readable instructions that, when executed by the computing system 200 (including the processing system 206), direct the processing system 206 to operate as described in herein in further detail, including to determine and effectuate a minimum ventilation amount when the $SpO_2$ value is below a threshold.

Although the computing system 200 as depicted in FIG. 2 includes one software 202 encapsulating one ventilation control module 21, it should be understood that one or more software elements having a single software module or more than two modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes at least one processor 207, which may be a microprocessor, a general purpose central processing unit, and application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and other elements within the system 1, such as elements of the ventilator circuit 14, the gas supply 27, the breathing circuit 16, the gas analyzer 90, the $SpO_2$ monitor 40, and/or the user interface 25. For example, the communication interface 208 receives the $EtCO_2$ measurements from the gas analyzer 90 and the $SpO_2$ values from the $SpO_2$ monitor 40. The communication interface 208 may also communicate control instructions to control the ventilator 10 to effectuate delivery of the determined ventilation amount to the patient. The communication interface may also communicate a control signal to the user interface 25 instructing display of the minimum ventilation amount, and/or instructing generation of an alert 100, such as to alert a clinician that the minimum ventilation mode has been engaged and/or that the $SpO_2$ value is unreliable.

The user interface 25, which includes a display device, is configured to receive input from a clinician, such as to adjust the $SpO_2$ threshold 70 and/or the predetermined waiting period 73. The user interface may also be configured to produce one or more alerts to the clinician. The alert 100 may include a visual alert on a digital display and/or an audio alert through speakers. The user interface 25 may include, in addition to the display device, a mouse, a keyboard, a voice input device, a touch input device (such as a touch pad or touch screen) for receiving a gesture from a user, a motion input device for detecting non-touch gestures and other motions by a user, and other comparable input devices and associated processing elements capable of receiving input from a user, such as a clinician. Speakers, printers, haptic devices and other types of output devices may also be included in the user interface 25.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A patient ventilation system comprising:
a ventilator configured to deliver ventilation gas to a patient;
a $CO_2$ concentration sensor configured to provide end tidal ($EtCO_2$) measurements for the patient;
an $SpO_2$ monitor configured to determine an $SpO_2$ value for the patient;
a ventilation control module executable on a processor and configured to:
compare the $SpO_2$ value to a threshold $SpO_2$ for inadequate oxygenation;
determine that the comparison indicates inadequate oxygenation;
set a minimum ventilation amount upon the comparison indicating inadequate oxygenation;
determine a ventilation amount based on the $EtCO_2$ measurements; and
control the ventilator based on the ventilation amount or the minimum ventilation amount, whichever is greater, so as to deliver at least the minimum ventilation amount to the patient while the $SpO_2$ value indicates inadequate oxygenation.

2. The system of claim 1, wherein the ventilation control module is further executable to determine the minimum ventilation amount based on a ventilation amount at a time of determining that the $SpO_2$ value indicates adequate oxygenation.

3. The system of claim 1, wherein the ventilation control module is further executable to determine the minimum ventilation amount based on historical ventilation information for the patient.

4. The system of claim 3, wherein the ventilation control module is further executable to determine the minimum ventilation amount based on a ventilation amount delivered prior to a time of determining that the $SpO_2$ value indicates inadequate oxygenation.

5. The system of claim 1, wherein the ventilation control module is further executable to:
monitor $SpO_2$ during a predetermined waiting period; and
determine that the $SpO_2$ value does not indicate adequate oxygenation within the predetermined waiting period prior to setting the minimum ventilation amount.

6. The system of claim 5, wherein the ventilation control module is further executable to determine that the $SpO_2$ value did not indicate adequate oxygenation during the predetermined waiting period prior to setting the minimum ventilation amount.

7. The system of claim 1, wherein the ventilation control module is further executable to, if no SpO$_2$ value received within a predetermined waiting period indicates adequate oxygenation, control the ventilator based on the ventilation amount and the minimum ventilation amount to deliver at least the minimum ventilation amount to the patient.

8. The system of claim 1, wherein the ventilation control module is further executable to determine that the SpO$_2$ value did not indicate adequate oxygenation within a predetermined waiting period prior to setting the minimum ventilation amount.

9. The system of claim 1, wherein the threshold SpO$_2$ is a clinician-set threshold.

10. The system of claim 1, wherein the ventilation control module is further executable to determine the minimum ventilation amount as a minimum effective alveolar minute ventilation based on one or more minimum effective alveolar minute ventilation values previously set by the ventilation control module.

11. A method of controlling a ventilator to ventilate a patient:
receiving EtCO$_2$ measurements for the patient from a CO$_2$ concentration sensor;
receiving an SpO$_2$ value for the patient from an SpO$_2$ monitor;
at a processor executing a ventilation control module:
comparing the SpO$_2$ value to a threshold SpO$_2$ for inadequate oxygenation;
determining that the comparison indicates inadequate oxygenation;
setting a minimum ventilation amount upon the comparison indicating inadequate oxygenation;
determining a ventilation amount based on the EtCO$_2$ measurements; and
controlling the ventilator based on the ventilation amount or the minimum ventilation amount so as to deliver at least the minimum ventilation amount to the patient while the SpO$_2$ value indicates inadequate oxygenation.

12. The method of claim 11, further comprising determining, at the processor executing the ventilation control module, the minimum ventilation amount based on a ventilation amount at a time of determining that the SpO$_2$ value indicates inadequate oxygenation.

13. The method of claim 11 further comprising determining the minimum ventilation amount based on historical ventilation information for the patient.

14. The method of claim 13, further comprising determining the minimum ventilation amount based on a ventilation amount delivered prior to a time of determining that the SpO$_2$ value indicates inadequate oxygenation.

15. The method of claim 14, wherein the minimum ventilation amount is selected based on one or more minimum effective alveolar minute ventilation values previously set by the ventilation control module.

16. The method of claim 11, further comprising, at the processor executing the ventilation control module:
monitoring SpO$_2$ during a predetermined waiting period; and
determining that the SpO$_2$ value does not indicate adequate oxygenation within the predetermined waiting period prior to setting the minimum ventilation amount.

17. The method of claim 16, further comprising determining, at the processor executing the ventilation control module, that the SpO$_2$ value did not indicate adequate oxygenation during the predetermined waiting period prior to setting the minimum ventilation amount.

18. The method of claim 17, further comprising generating an alert to indicate that the minimum ventilation amount is set.

19. The method of claim 11, further comprising determining, at the processor executing the ventilation control module, that the SpO$_2$ value did not indicate adequate oxygenation within a predetermined waiting period prior to setting the minimum ventilation amount.

20. The method of claim 11, comprising receiving input from a clinician to set the threshold SpO$_2$ below 90 percent.

* * * * *